United States Patent [19]

Langley et al.

[11] Patent Number: 5,324,445
[45] Date of Patent: Jun. 28, 1994

[54] POLYMERIC COMPOSITIONS

[75] Inventors: John Langley, Guiseley; Kenneth C. Symes, East Morton, both of United Kingdom

[73] Assignee: Allied Colloids Limited, England

[21] Appl. No.: 734,545

[22] Filed: Jul. 23, 1991

Related U.S. Application Data

[63] Continuation-in-part of Ser. No. 398,083, Aug. 24, 1989, abandoned.

[30] Foreign Application Priority Data

Aug. 24, 1988 [GB] United Kingdom ................ 8820061
Aug. 24, 1988 [GB] United Kingdom ................ 8820062
May 14, 1991 [GB] United Kingdom ................ 9110408

[51] Int. Cl.$^5$ ............................................. C11D 3/386
[52] U.S. Cl. ............................ 252/174.12; 252/174.13; 252/DIG. 12
[58] Field of Search ................ 252/174.12, 174.13, 252/DIG. 12

[56] References Cited

U.S. PATENT DOCUMENTS 4,777,089 10/1988 Takizawa et al. ............... 252/174.11
4,906,396 4/1990 Falholt et al. ................... 252/174.12

Primary Examiner—Olik Chaudhuri
Assistant Examiner—C. Everhart
Attorney, Agent, or Firm—Ostrolenk, Faber, Gerb & Soffen

[57] ABSTRACT

A liquid composition is disclosed which comprises a substantially stable dispersion in a liquid phase of particles comprising a detergent enzyme and a protective polymeric material that is impermeable to liquid detergent concentrates but releases the enzyme when agitated in aqueous wash liquor and comprises an outer polymeric shell and/or a polymeric matrix through which the enzyme is distributed.

20 Claims, No Drawings

POLYMERIC COMPOSITIONS

The application is a continuation in part of application Ser. No. 398,083 filed Aug. 24, 1989, now abandoned, by John Langley and Kenneth Charles Symes.

This invention relates to the encapsulation of particles containing an active ingredient, for example an enzyme, that is to be protected from the liquid or other medium that surrounds the particles.

It is well known to include enzymes in detergent compositions in order to improve their performance. The enzymes will be de-activated by exposure to other chemical components in the detergent, and possibly also upon exposure to moisture. It is therefore necessary to protect the enzyme, for instance by encapsulation within a polymer. Detergent powders therefore frequently contain powdered enzyme-polymer compositions.

A difficulty that exists with liquid detergents is that the liquid phase of the detergent concentrate is more likely to attack the encapsulating polymer and does, in any event, tend to provide a more rigorous chemical and physical environment from which the polymer has to protect the enzyme. It has proved difficult to provide the enzyme in a protected form and that is stably distributed within the liquid detergent. If the enzyme is not fully protected then the enzyme activity in the detergent, when it is used by the consumer, will be very low.

In GB 2,186,884 and U.S. Pat. No. 4,906,396 it is proposed to disperse the enzyme in a silicone oil and to disperse this dispersion in the liquid detergent. Although it is proposed that the dispersed particles can have a size as low as 2 $\mu$m in practice they are always very much larger than this. This has to follow from the fact that the enzyme, that is within the dispersed particles, is stated to have a particle size that is preferably above 5 $\mu$m, with the result that the dispersed particles containing the enzyme must inevitably be much larger. In practice therefore at least 90% of the particles of oil and enzyme will always have a particle size substantially above 5 $\mu$m.

In JP-A-63-105098 it is proposed to microencapsulate enzyme in polyvinyl alcohol and to disperse the resultant microcapsules in a liquid or gel detergent. In practice any liquid detergents that are used would need to have a high viscosity because the microcapsules that are made are always relatively large, for instance 150 to 800 $\mu$m in example 1 and so would inevitably settle out from a conventional, relatively low viscosity, liquid detergent concentrate. One way that is described for making the microcapsules involves dispersing an enzyme solution containing polyhydroxy compound and polyvinyl alcohol is dispersed in hydrophobic solvent as microdroplets and the water content is removed by heating or decrease in pressure. As mentioned, the particle size is large and this process is not exemplified.

The commercial reality is that there is no entirely satisfactory way of incorporating detergent enzymes into liquid detergent concentrates and, in particular, the enzymic activity of any such composition is rapidly lost during storage.

It would be desirable to be able to provide a liquid composition that can be incorporated into a liquid detergent concentrate, and it would be desirable to provide such concentrates wherein the enzymic activity can be maintained.

A liquid composition according to the invention comprises a substantially stable dispersion in a liquid phase of particles comprising a detergent enzyme and a protective polymeric material that is impermeable to liquid detergent concentrates but releases the enzyme when agitated in aqueous wash liquor and that comprises an outer polymeric shell and/or a polymeric matrix through which enzyme is distributed, and in this composition the particles have a size below 20 $\mu$m and have been made by a process comprising (a) forming a dispersion of an aqueous liquid phase containing the enzyme in a water immiscible liquid in the presence of a dispersion stabiliser and azeotroping the dispersion, and/or (b) forming an outer polymeric shell by coacervation.

Preferably, the particles according to the invention comprise a polymer shell which is formed by coacervation, and generally also include the polymeric matrix.

Therefore, the invention further provides a composition and a process for the preparation of coacervated particles comprising providing an aqueous solution of coacervating polymeric material that can be caused to precipitate as a coacervate about particles dispersed in the solution, providing a substantially anhydrous dispersion in oil of particles of a matrix polymer containing an active ingredient, dispersing this substantially anhydrous dispersion of matrix polymer particles containing the active ingredient into the aqueous solution and causing a coacervate shell to form around the droplets of the matrix particles, wherein the matrix polymer partitions into the oil in preference to the aqueous solution of coacervating polymeric material.

Part at least of the process for making the composition of the invention preferably comprises forming a dispersion of an aqueous phase containing the enzyme in a water immiscible liquid in the presence of the dispersion stabiliser and azeotroping the dispersion. The azeotroped produced may serve as the liquid composition, in which event the liquid phase of the composition is the water immiscible liquid in which the dispersion was formed. The particles in this dispersion (and in the final product) are preferably below 10 $\mu$m, most preferably below 3 $\mu$m. This assists the formation of a stable dispersion.

The dispersion stabiliser that is used in this process is preferably an amphiphatic polymeric stabiliser, that is to say a polymeric stabiliser having hydrophobic and hydrophilic components as a result of having been made from hydrophobic and hydrophilic monomers. Accordingly, the particles of the dispersion each have a surrounding hydrophobic film derived from the hydrophobic units in the stabiliser and this hydrophobic film can serve as part or all of the protective polymeric material. The formation of the initial dispersion, that is subjected to azeotroping, is generally facilitated by the incorporation of a water-in-oil emulsifier, and the hydrophobic groups of this may also contribute to the formation of a protective hydrophobic film around each particle.

Generally, however, it is necessary to include additional polymeric material in order to provide adequate protection. This additional material can be a polymeric matrix for each particle, with the enzyme being distributed through the matrix. The matrix may be of uniform composition throughout, but preferably it is chemically modified during or after the formation of the matrix (i.e., during or after the azeotroping) so as to render it less permeable to liquid detergent concentrate. Thus the polymer may be introduced in soluble form and may then be insolubilised, particularly at the outer surface layer of the matrix.

Instead, and usually in addition to, having a matrix polymer, it is also possible to provide an outer polymeric shell. This can be formed by any suitable microencapsulation technique but, in the invention, it is particularly preferred that it is formed by coacervation. Coacervation is usually conducted in an aqueous phase and so the liquid phase of the composition of the invention can be this coacervating liquid phase, provided the polymeric shell is sufficiently impermeable to it during storage.

The liquid compositions of the invention also include compositions wherein the liquid phase is the continuous phase of a liquid detergent concentrate, and it is then preferred that the active ingredient is a detergent enzyme. The detergent composition may be formulated in conventional manner from appropriate blends of surfactants, builders and other conventional additives for liquid detergents.

The liquid detergent is normally a relatively low viscosity liquid that has a low water content and a high content of surfactant and/or electrolyte. Many polymeric materials, particularly if they are addition polymers made from a monomer or monomer blend containing ionic monomers, are much less soluble and permeable when exposed to high electrolyte or surfactant concentrations than when exposed to dilute aqueous solutions. Because of this, and because of the small particle size of the particles, it is therefore possible to provide the enzyme in a protective polymer that is substantially impermeable to the other components of the liquid detergent but which will dissolve when the water content is increased greatly, namely when the concentrate is diluted into the wash liquor for use. Although the dilution effect alone may be sufficient to release the enzyme from within the particles, reliance may also be placed on the temperature of the wash liquor, since this is generally above 30° C. and usually above 40° C. and so is above the normal storage temperature of the composition. In particular, reliance may be placed on agitation, for instance of the sort to which aqueous wash liquors are normally subjected, since this can promote rupture of the polymeric matrix or, especially, of any outer protective polymeric shell.

The enzyme can be any enzyme that is useful in detergents. It is preferably a protease, especially an alkaline protease, but it may for instance be an amylase or a lipase. It may be introduced initially in powder form but is generally introduced as a solution (or a dispersion containing cellular material with which it was initially produced). This solution may be formed from a dried enzyme product or it may be a fermentation liquor, for instance the fermentation broth in which the enzyme was produced initially or a concentrate obtained from that. Processes in which the enzyme is provided initially as a fermentation broth are described in U.S. application Ser. No. 398,057 filed Aug. 24, 1989 and now U.S. Pat. No. 5,035,900.

The preferred products of the invention are made by a process that involves reverse phase azeotroping, and for this purpose an aqueous phase containing the enzyme is dispersed in a water immiscible liquid in the presence of the dispersion stabiliser. The aqueous phase should be stable both against phase separation and against loss of activity of the enzyme. For instance it can be desirable to include a polyhydroxy compound, especially sucrose or other sugar or a glycol or other low molecular weight polyhydroxy compound, e.g., propylene glycol. The dispersion of the aqueous phase into the water immiscible liquid is generally accompanied by shear and is conducted in the prescence of a water-in-oil emusifier so as to promote the formation of small particles generally having a size below 10 $\mu$m, most usually below 3 $\mu$m. Suitable surfactants, water immiscible liquids and polymeric stabilisers, and suitable azeotroping conditions, are described in EP 0128661 and 0126528 and, in particular, suitable stabilisers are described in GB 2,002,400 with particularly preferred stabilisers being described in GB 2,001,083 and GB 1,482,515.

The immiscible liquid is non-aqueous and must include liquid that will form an azeotrope with water. Often the water immiscible liquid is a blend of a relatively high boiling liquid that remains in the dispersion and a low boiling liquid that is azeotroped from the dispersion. The temperature at which azeotroping occurs is generally below 100° C. and is controlled by the choice of liquid and, especially, the pressure at which the distillation is conducted. Generally the distillation is conducted under reduced pressure and when the active ingredient is temperature sensitive (e.g., an enzyme) the reduced pressure is preferably such that the azeotroping occurs at a maximum temperature of not more than 80° C., often below 70° C. and most preferably below 50° C. For instance by applying a relatively high vacuum it is possible to azeotrope at very low temperatures, for instances as low as 30° C. Sodium sulphate or other salt may be added to lower the azeotroping temperature.

The polymer should be film forming at the distillation temperature, and usually is film forming at 20° C. or lower. The azeotroping should be conducted to render the particles substantially dry so that they are not desensitised by the presence of water in them. In practice this means that the water content is generally below 25%, and preferably below 10%, by weight of the particles and most preferably is at or, especially, below the moisture content that would prevail if the particles were exposed to the atmosphere.

The aqueous phase containing the enzyme preferably contains a polymer so as to form a solid polymeric matrix through which the active ingredient is distributed.

The solid polymer of the matrix can be a natural or modified polymer such as a starch or a cellulose (e.g., carboxy methyl cellulose) or gum. Preferably it is a synthetic polymer formed from an ethylenically unsaturated water soluble monomer or monomer blend, which may be non-ionic or ionic.

Suitable anionic monomers are ethylenically unsaturated carboxylic or sulphonic monomers, most preferably monomers such as (meth) acrylic acid, crotonic acid, itaconic acid, maleic acid, (meth) allyl sulphonic acid, vinyl sulphonic acid and 2-acrylamido-2-methyl propane sulphonic acid. Acrylic or methacrylic acid is preferred.

Suitable cationic monomers are dialkylaminoalkyl (meth) -acrylamides and, preferably, -acrylates, usually as acid addition or quaternary ammonium salts. Particularly preferred are monomers such as diethylaminoethyl (meth) acrylate.

Suitable non-ionic monomers of this type are (meth) acrylamide and hydroxy-lower alkyl (meth) acrylates.

The anionic and cationic monomers may be either in the free acid or free base form when they are sufficiently soluble in this form (for instance acrylic acid) but more usually in the form of an alkali metal or ammonium salt of anionic monomers or an acid addition or quaternary ammonium salt of cationic monomers.

The polymer may be polyvinyl pyrollidone, polyvinyl alcohol or ethylene (meth) acrylic acid copolymer.

The preferred polymer is usually based on 0–50% acrylamide and 50–100% acrylic acid or soluble salt thereof.

The solid polymer of the matrix is generally soluble in water and may have been made by any conventional polymerisation technique, such as reverse phase suspension polymerisation, solution polymerisation, reverse phase bead polymerisation or gel polymerisation. Alternatively, the polymer may be a copolymer of soluble and insoluble monomers (e.g., methacrylic acid and ethyl acrylate) and may have been made by oil-in-water emulsion polymerisation followed by addition of sodium hydroxide or other alkali to convert it to a soluble form.

Instead of introducing the polymer in a soluble form, the polymer can be a polymer that is insoluble in water but is soluble in alkali and which is introduced as an oil-in-water emulsion that has been made by emulsion polymerisation of ethylenically unsaturated monomer or monomer blend that is insoluble in the water phase of the polymerisation mixture. The monomers are generally a blend of anionic solubilising monomers (typically selected from the anionic monomers discussed above) and ethylenically unsaturated non-ionic monomers, the overall blend being insoluble at the pH of the emulsion. Thus the emulsion polymerisation may be conducted at a pH below 7 but when the polymer is subsequently exposed to more alkaline conditions the polymer becomes soluble (or highly swellable). Suitable non-ionic water insoluble monomers include alkyl (meth) acrylates, styrene, acrylonitrile, vinyl chloride, vinyl acetate or vinyl butyl ether. Ethyl acrylate is preferred, with the polymer preferably being formed from 10 to 70% methacrylic acid or other anionic monomer, 10 to 70% ethyl acrylate or other insoluble monomer and 0 to 70% acrylamide or other soluble non-ionic monomer.

The use of an emulsion polymer of this type is of particular value when it is desired for the polymeric matrix to permit substantially no release of the biological material in one environment (for instance neutral or acidic) and rapid release in an alkaline environment.

Controlled release of enzyme can also be obtained when the polymer is introduced initially as a salt with a volatile amine (for instance ammonia) of a polymer derived from ethylenically unsaturated carboxylic acid monomer such as (meth) acrylic acid. The salt is soluble in water but the ammonia or other volatile amine evaporates during the azeotroping to render the polymer less hydrophilic. Accordingly at least the outer shell of the particles, and possibly substantially the entire polymeric matrix, will be less hydrophilic and water soluble than when the carboxylic groups are in alkali or amine salt form. The particle therefore has relatively low permeability to ambient moisture but, upon exposure to a slightly alkaline aqueous solution (for instance as typically prevails in a wash liquid) the polymer will be sufficiently solubilised to permit rapid release of the trapped enzyme or other biological material. For this purpose the polymer is preferably based on 0 to 50% acrylamide and 50 to 100% acrylic acid or, preferably, methacrylic acid. Products of these types are described in more detail in our copending U.S. application Ser. No. 398,088 filed Aug. 24, 1989.

The matrix polymer preferably is a polymer that is useful as a component in a detergent, for instance as a detergent builder or detergent anti-redeposition aid. Suitable polymers include carboxy methyl cellulose and anionic synthetic polymers, for instance polymers of molecular weight 4,000 to 300,000 and formed from water soluble ethylenically unsaturated carboxylic or sulphonic monomer, optionally with water soluble non-ionic monomer. Preferably the polymer is of sodium polyacrylate but copolymers with acrylamide and homopolymers or copolymers with, for instance, allyl sulphonate or 2-acrylamido methyl propane sulphonate may be used. Copolymers of maleic anhydride with, for instance, acrylic acid are also suitable.

It is preferred that the amount of polymer should be at least 0.5 times the amount of active ingredient (on a dry weight basis). Preferably there is an excess of polymer, for instance at least two times the amount of active ingredient and preferably there is a large excess, for instance at least seven times. The use of this seven-fold excess (or more) of polymer means that the biological material is protected very effectively from the environment and even if the particles are damaged the amount of active ingredient that is liable to be exposed to, or escape into, the environment is very low. Generally the amount of polymer is at least 10 times and usually at least 15 times the amount of active ingredient (on a dry weight basis). It is usually unnecesary for it to be more than 50 times, and amounts in the range 15 to 30 times are often suitable although amounts up to 100 times or more can be used.

Small amounts of filler and other additives can be included in the matrix. Generally the polymeric material constitutes at least 50%, preferably at least 75% and most preferably at least 90% by weight of the solid composition formed of a matrix, active ingredient and any inert material distributed through the matrix.

It is generally preferred that the aqueous phase that is to be dispersed and then azeotroped should be formed from the enzyme and preformed polymer. However if desired it can be made by polymerising the appropriate monomer or monomer blend in the presence of the active ingredient so as to form the polymer in the presence of the active ingredient. Alternatively, reactive polymer can be used, e.g., as in EP-A-032831 and can be reacted in the matrix or shell.

The product resulting from the azeotroping is a stable dispersion in the water immiscible liquid of substantially dry particles of which at least 90% by weight of which are preferably below 3 μm, often below 2 μm and frequently even below 1 μm.

The polymeric particles will, in practice, generally have an absorbed layer of hydrophobic material due to emulsifier and/or polymeric stabiliser.

The matrix polymer is preferably chemically modified at least at its outer surface either during or after the azeotroping. For instance a volatile amine salt can be converted to a less volatile free acid compound or the polymer can be subjected to external chemical reaction. For instance if the polymer is formed of chitosan it can be acetylated, or otherwise esterified, so as to insolubilise it. Various other insolubilisation reactions can be conducted on water soluble polymers in known manner so as to render them less soluble or wholly insoluble in water. The necessary reagent for this reaction is preferably included in the dispersion during the azeotroping stage. For instance the surface can be subjected to cross linking.

Instead of, or in addition to modifying the matrix polymer, a polymeric shell can be formed by coacervation. Coacervation techniques are, of course, known for encapsulating a variety of materials and are described in, for instance, GB 1,275,712, 1,475,229 and 1,507,739 and DE 3,545,803.

It is possible, in the invention, to form a coacervate polymeric shell about active ingredient, for instance, dried enzyme particles by techniques such as those described in the above-mentioned patents. Preferably however a dispersion of enzyme particles in a water immiscible liquid (with the enzyme preferably being distributed throughout a polymeric matrix) is preferably formed by azeotroping as described above, and then an emulsion of droplets of the dispersion is formed in an aqueous medium and the droplets are coated by coacervation with polymeric material while dispersed in the aqueous medium to form a coacervate dispersion.

The coacervated particles are preferably stabilised against agglomeration while dispersed in the aqueous medium. This can be achieved by the addition of appropriate stabilising agents but preferably the materials used for forming the coacervate are such as to stabilise the coacervated particles against aggregation. Thus preferably the emulsification of the dispersion into the aqueous coacervating medium is conducted in the absence of any emulsifying agent, adequate initial stability be provided by the coacervating polymer or polymers in the coacervating system and final resistance against agglomeration being provided by the coacervate shell.

Although a coacervate coating can in some instances be formed by precipitation of a single polymer around the emulsified particles it is preferably formed by physical or chemical interaction between the two or more coacervating polymers in the aqueous medium into which the solution of enzyme (and usually matrix polymer) has already been dispersed, for instance to resemble an emulsion. As is known, when two coacervating polymers interact in the presence of an emulsion they tend to form a coating around the individual particles of the emulsion. However any other way of forming a stabilising polymeric coating on the particles by coacervation can be used. For instance a fine particulate coacervate can be formed in an aqueous medium in the absence of the emulsified particles and can then be contacted with the emulsified particles, either by emulsifying the organic solution into the aqueous medium containing the particulate coacervate or by blending that aqueous medium with an aqueous medium containing the emulsified particles. A method of this general type is described in DE-A-3,545,803 (except that it is not essential to react the coacervate coating subsequently with non-ionic melamine formaldehye).

The coacervate-forming polymers that will interact to form a coacervate are generally counterionic. At least one of the polymers may be amphoteric. Particularly preferred polymers are blends of cationic formaldehyde polymer (generally cationic urea formaldehyde) and anionic acrylamide polymer. Suitable materials are described in, for instance, DE-A-3,545,803, GB 2,073,132 and 1,507,739 and U.S. Pat. No. 4,100,103.

For the purposes of the present invention, it is usually sufficient merely to form the dispersion-stabilising coacervate coating around the fluid particles and it is usually unnecessary to react this further by cross linking or condensation with, for instance, further formaldehyde polymer, as is suggested in each of those patents.

Provided the emulsification of the dispersion droplets into the aqueous coacervating medium is conducted with only low amounts of shear and/or in the substantial absence of oil-in-water emulsifier, it is possible to form an emulsion of droplets of the dispersion in the aqueous medium and the eventual coacervated particles will then each consist of the outer coacervated shell, one or more of the enzyme particles, generally being matrix particles having enzyme distributed throughout, and an inner hydrophobic shell between these particles and the outer shell. This inner hydrophobic shell can consist solely of the original water immiscible liquid but preferably the water immiscible liquid that is encapsulated comprises a blend of a relatively volatile liquid and a less volatile hydrophobic material, and the relatively volatile liquid is evaporated from the particles during or after coacervation.

The evaporation can be conducted by distillation at atmospheric or reduced pressure and is generally conducted as an azeotropic distillation. This is generally conducted under reduced pressure. By appropriate selection of the solvent and the pressure at which distillation is conducted it is possible to effect the distillation at low temperatures, e.g., as low as 50° C. or even as low as 30° C. It can be convenient to add appropriate volatile liquid and/or less volatile liquid to the azeotroped dispersion from the first stage, before the coacervation. The less volatile hydrophobic material can be either a high boiling oil or can be a solid or semi-solid material, for instance to form a wax layer around the enzyme particles.

The invention has been described above for the protection of enzymes. However it can also be applied to the protection of a wide variety of other active ingredients that are unstable to a surrounding liquid or gaseous atmosphere.

As described above it can be desirable for the matrix polymer to be a salt formed between ammonia or other volatile amine and a polymer derived from ethylenically unsaturated carboxylic acid. The matrix polymer can be formed or introduced as an aqueous solution of the salt with the volatile amine as a reverse phase dispersion of polymer particles in the oil, and this dispersion can then be subjected to azeotroping to drive off water and the volatile amine, so as to convert the polymer wholly or partially to the free acid form. This will be less hydrophilic and less water soluble than the starting polymer and so the particle has lower permeability to ambient moisture. As a result, there is less tendency for moisture to permeate into the matrix or for water soluble active ingredient that is in the matrix to permeate out of the matrix.

The presence of the coacervate shell around the matrix should reduce still further the tendency of such permeation to occur. However the system is not entirely satisfactory for a number of reasons.

One problem is that the steps involved in forming the coacervate coating generally involve homogenising the polymer-in-oil dispersion into the aqueous solution of coacervating polymer or polymers, and this homogenisation can result in sufficiently intimate and prolonged contact between the matrix polymer and the aqueous solution that, even when the matrix polymer is in its relatively insoluble form, there can be significant migration of water into the matrix. If the coacervate shell is, or becomes, sufficiently impermeable to prevent permeation of water, the core will remain moist and this can be very undesirable for some active ingredients (e.g. enzymes). Additionally, during the homogenisation there can be migration of water soluble active ingredient out of the matrix. Further, the homogenisation tends to result in the encapsulation of some particles that are substantially free of polymeric matrix and some particles that are substantially free of oil.

It would be desirable to be able to provide coacervated particle that could more reliably protect any active ingredient in the matrix from exposure to moisture during manufacture and subsequent storage.

The invention also provides a particulate composition that comprises particles having
 a substantially anhydrous core comprising a matrix polymer containing active ingredient,
 an inner shell of hydrophobic oil around the core and
 an outer shell of coacervated polymer around the inner shell,
wherein the matrix polymer is sufficiently hydrophobic that it will partition preferentially into the oil rather than water or an aqueous solution, and in particular the aqueous solution from which the coacervate polymer was formed.

If the coacervate polymer was prepared from a neutral solution, then it is more convenient to define the matrix polymer as partitioning into the oil in preference to water, but if the coacervate polymer was formed from, for instance, an alkaline solution then the relative partitioning effect should be determined with respect to an alkaline solution corresponding to the alkalinity of the coacervating polymer (in order to allow for any solubilisation of the polymer by salt formation with the alkali of the coacervating solution).

A process according to the invention for producing coacervated particles comprises
 providing an aqueous solution of coacervating polymeric material that can be caused to precipitate as a coacervate about particles dispersed in the solution,
 providing a substantially anhydrous dispersion in oil of particles of a matrix polymer containing active ingredient.
 dispersing this substantially anhydrous dispersion of matrix polymer particles containing active ingredient into the aqueous solution, and causing a coacervate shell to form around the droplets of the matrix particles,
wherein the matrix polymer partitions into the oil in preference to the aqueous solution of coacervating polymeric material.

In a preferred process of the invention, the substantially anhydrous dispersion of particles of the matrix polymer in oil is made by providing a dispersion in oil of an aqueous solution of matrix polymeric material containing active ingredient, subjecting this dispersion to distillation to provide a substantially anhydrous dispersion in oil of particles of matrix polymer containing active ingredient, and during or after the distillation chemically modifying the matrix polymer to produce a polymer that is insoluble in water and that will partition into the oil in preference to the aqueous solution of coacervating material.

In one process of the invention, the initial aqueous solution of matrix polymeric material is made by dissolving the polymeric material in water or other aqueous solution in which it is soluble, and dispersing or dissolving the active ingredient in the solution. In another process, the dispersion is made by reverse phase polymerisation of water soluble polymeric material from a water soluble monomer or monomer blend in the presence of the active ingredient.

By saying that the matrix polymer partitions into the oil in preference to the aqueous solution of coacervating polymer, or other water phase, we mean that the polymer particles will be preferentially attracted to the oil phase rather than to the aqueous phase. One simple way of demonstrating whether or not the matrix polymer does preferentially partition into the oil phase is to incorporate some water soluble dye into the matrix polymer and then to disperse vigorously into the aqueous phase a dispersion of the dyed polymer particles in the oil, and then to allow the dispersion to phase separate. If substantially all the dye has remained in the polymer particles, this shows that there was substantially no contact between the polymer particles and the water, and that the polymer particles therefore partition preferentially into the oil phase. However if the water phase is significantly dyed, this shows that the polymer particles have partitioned significantly or preferentially into the aqueous phase.

The oil can be any hydrophobic, water immiscible, liquid. Examples are aliphatic, cycloaliphatic, aromatic and naphthenic oils, vegetable oils and silicone oils.

Because the oil is hydrophobic, and because the matrix polymer also is hydrophobic and is attracted to the oil in preference to the water, a film or larger amount of oil is held around each polymer particle during the formation of the coacervate, and the coacervate coating is formed as an outer shell around this inner shell of oil. This has two significant advantages:

Firstly, there is little or no direct contact between the aqueous coacervating phase and the substantially anhydrous matrix polymer. As a result, there is little or no opportunity for water to migrate into the substantially anhydrous matrix polymer during the formation of the coacervate coating or for active ingredient in the matrix polymer to migrate out into the coacervating solution. In particular, the coacervation can be conducted without raising the moisture content of the matrix polymer.

Secondly, the active ingredient in the matrix polymer is protected from its surroundings not only by the outer coacervate coating but also by the inner layer of hydrophobic oil. Thus even if the coacervate coating has a tendency to allow permeation by moisture, the inner shell of hydrophobic oil between the coacervate and the matrix polymer will reduce or eliminate any risk of transfer of moisture from outside the particle to the matrix polymer or transfer of water soluble active ingredient in the matrix polymer to outside the coacervate coating.

Since it is preferred that the matrix polymer partitions preferentially into oil, it is preferred for it to be much more hydrophobic than for instance the acrylic acid ammonium acrylate polymer proposed above.

As mentioned above, the partitioning matrix polymer is generally provided by insolubilising a polymer that was initially provided as an aqueous solution. Any modification that achieves this insolubilisation can be used but preferably the modification is reversible, so that the polymer can then be solubilised when it becomes necessary to facilitate release of active ingredient from within the particles into water. The modification can be achieved chemically or physically. When the modification is achieved chemically, the initially soluble polymer is preferably a copolymer of water soluble ionic monomer with water insoluble monomer, in which event the reversible insolubilisation will preferably comprise converting some or all of the ionic monomer groups to free acid or free base monomer groups. Suitable anionic monomer groups are ethylenically unsaturated sulphonic or, preferably, carboxylic acid groups. Preferred monomers include methacrylic and acrylic acids. The anionic groups may be present in the soluble polymer as alkali metal or amine salts and may be converted to free carboxylic acid groups in the insolubilisation reaction. This can be achieved by acidification with hydrochloric acid or other suitable acid but preferably the anionic group is present as a salt of a volatile amine (e.g., ammonia) and the acidification is achieved by heating the polymer sufficient to volatilise the ammonia or other amine. This heating can occur during the distillation step. Although anionic groups are preferred as the ionic groups, cationic groups such as dialkylaminoalkyl(meth)-acrylate or amide acid addition or quaternary ammonium salt can be used.

The ionic groups must be copolymerised with hydrophobic ethylenically unsaturated monomer. Suitable hydrophobic ethylenically unsaturated monomers are hydrocarbon monomers such as styrene and alkyl-substituted styrenes, alkyl acrylates and methacrylates (for instance methacrylate) and vinyl acetate.

The amount of hydrophobic monomer will generally be from 40 to 95% by weight, with the balance to 100% being the ionic monomer. However small amounts (e.g., up to 20%) of other monomers that are neither ionic nor hydrophobic may be included, examples being vinyl pyrrolidine.

The matrix polymeric material can be made by solution polymerisation in the organic solvent or by oil-in-water emulsion polymerisation, followed by addition of sufficient alkali to solubilise the aqueous solution in the conventional manner. Active ingredient can be dispersed or dissolved in the polymerising mixture before polymerisation, but preferably is dispersed or dissolved into a solution of the polymeric material after polymerisation.

If the polymer was not formed as a reverse phase emulsion, the resultant solution of polymer containing active ingredient can be dispersed into the desired hydrophobic oil (or the polymer can be dispersed in the oil and the active ingredient then added) in the presence of suitable dispersion stabiliser that can be a water-in-oil emulsifier and/or an amphipathic polymeric stabiliser. Suitable emulsifiers, stabilisers and oils are described in, for instance, EP 128661, EP 284366 and EP 284367. Emulsification can be achieved by homogenisation with a Silverson or other homogeniser and the product can subsequently be subjected to distillation under reduced pressure until substantially all the water has been removed. If the active ingredient is temperature sensitive, the reduced pressure should be sufficiently low that the distillation occurs at a safe temperature, for instance below 30° C. The anionic monomer is preferably present as ammonium salt, in which event the dispersion can be heated briefly to a temperature and for a time sufficient to drive off most of the ammonia but insufficient to damage any heat-sensitive active ingredient in the matrix polymer.

Alternatively, the resultant dispersion of dry polymer particles in oil can then be dispersed into an aqueous solution of coacervating polymeric material, for instance by emulsification using a Silverson homogeniser. The particle size can be controlled in known manner by appropriate selection of the emulsification conditions and generally is below 20 μm, usually below 10 μm, although if desired the process can be used to make larger particles, for instance up to 100 μm.

When the particles comprise a substantially anhydrous core comprising a matrix polymer containing active ingredient surrounded by an inner shell of hydrophobic oil, and an outer shell of coacervated polymer around the inner shell, coacervation can be by any of the techniques described above, but is preferably by use of "low critical solution temperature" (LCST) polymers. Coacervation can be brought about solely by heating as described in U.S. Pat. No. 3,244,640 but preferably coacervation is brought about by heating following by the addition of salt.

When it is desired to release the active ingredient from within the matrix polymer, the coacervate particles are exposed to conditions whereby alkali can permeate through the coacervate coating and gradually migrate through the oil phase so that it can react with the matrix polymer to solubilise that.

When the insolubilisation is achieved by physical modification, the effect is preferably achieved by alteration of the temperature and/or electrolyte concentration. Preferably the polymer is a "low critical solution temperature" (LCST) polymer. A characteristic of such polymers is that they can be in aqueous solution at one temperature but can be insolubilised reversibly by heating to a higher temperature.

The LCST polymer can be a naturally occurring polymer such as certain cellulose derivatives, such as the methyl, hydroxy propyl, and mixed methyl/hydroxy propyl cellulose ethers. However it is generally preferred for the LCST polymer to be a synthetic polymer formed by polymerisation of what can be termed an LCST monomer either as a homopolymer or as a copolymer with a hydrophilic monomer that is present in an amount insufficient to cause T1 to be unacceptably high. Suitable LCST monomers include N-alkylacrylamides, N,N-dialkylacrylamide, diacetone acrylamide, N-acryloylpyrrolidine, vinyl acetate, certain (meth) acrylate esters especially hydroxypropyl esters), styrene, and various other vinyl monomers, especially N-vinylimidazoline and the like. Hydrophilic monomers that can be copolymerised with these include acrylamide, hydroxyethyl acrylate, vinyl pyrollidone, or hydrolysed vinyl acetate.

Anionic or cationic monomer can be used in place of or in addition to the above listed comonomers to form a copolymer or terpolymer with the LCST polymeric component respectively. Suitable, anionic monomers include ethylenically unsaturated carboxylic or sulphonic acid monomers, for example (meth) acrylic acid and alkaline salts thereof, and 2-acrylamido methyl propane sulphonic acid. Suitable cationic monomers include dialkylaminoalkyl (meth) acrylates and -acrylamides as acid addition or quaternary ammonium salts, for example dialkylaminoethyl (meth)acrylate acid addition salts.

Preferably the polymer becomes insoluble and comes out of its aqueous solution at a temperature of at least 25° C., e.g. 45° to 80° C., or even up to 100° C. Electrolyte can be included in the solution to lower the temperature of insolubilisation or can be added after insolubilisation to lower the temperature of resolubilisation. Thus the active ingredient can be mixed into aqueous polymer solution, this can then be dispersed, into oil which is sufficiently warm to insolubilise the matrix, the oil dispersion can be distilled to form an anhydrous dispersion, and this can be coacervated as before but at a temperature that is sufficiently high to prevent solubilisation. The conditions and materials for dispersing the aqueous polymer into oil and for forming the coacervate may be broadly the same as for the polymers that are to be insolubilised chemically. Release can occur by contact with water or aqueous solution at which the LCST matrix polymer is adequately soluble.

Active ingredients that may be encapsulated by the techniques described herein include other biologically produced materials such as enzymes or cellular material or chemically produced material that is unstable when exposed to moisture or other ambient conditions. However the invention is of particular value when applied to enzyme or other active ingredients that are to be dispersed in a liquid detergent concentrate since the outer shell of coacervate polymer and the inner shell of oil will protect the insoluble polymer and active ingredient from the components of the detergent concentrate, but when this concentrate is diluted in water and agitated the coacervate coating will disintegrate and the aqueous detergent solution will tend to strip the oil off the polymer particles and will provide a solution having sufficient alkalinity to solubilise the matrix polymer so as to promote release of active ingredient from within the matrix polymer. The invention is therefore of particular benefit for the encapsulation of detergent enzymes.

Suitable proportions of active ingredient: matrix polymer are 1:100 to 1:0.5 on a dry weight basis, whilst the matrix/active ingredient:coacervate polymer ratio is generally from 1:60 to 5:1 on a dry weight basis. The amount of oil encapsulated within the particles is generally from 20 to 97% based on the dry weight of the particles.

The following are examples.

EXAMPLE 1

A 25% aqueous solution of ammonium polyacrylate having molecular weight 30,000 is blended with sufficient of a detergent alkaline protease to give a polymer:enzyme dry weight ratio of 19:1. This solution is stirred into a parafinic oil in the presence of a water-in-oil emulsifier and an amphipathic polymeric stabiliser using sufficient shear to form a stable emulsion in the oil of particles having a size below 3 μm and consisting of the aqueous blend of polymer and enzyme.

This emulsion is then be subjected to azeotropic distillation under reduced pressure such that the maximum temperature in the emulsion does not exceed about 50° C., and results in a dispersion in the oil of substantially dry particles having a size below 3 μm, often below 1 μm, each consisting of a matrix of water soluble polymer, mainly in the free cid form, throughout which the enzyme is uniformly distributed.

This dispersion is stirred gently into a conventional high-surfactant, high-electrolyte, low-water domestic clothes detergent to form a dispersion of the substantially individual polymer-enzyme particles in the detergent. These particles may remain substantially stable during storage but upon dilution with water the polymer will dissolve to expose the enzyme to the other components in the detergent.

EXAMPLE 2

The dispersion of enzyme-polymer matrix particles in parrafin oil is obtained as in example 1.

A solution of 168 g of 20% aqueous acrylamide/sodium acrylate polymer is dissolved in 600 g water and 76 g of a 35% urea/formaldehyde resin is dissolved in 100 g water and is added over a period of 20 seconds while stirring with a Silverson stirrer, stirring then being continued for a further 30 seconds. 120 g of the dispersion in parrafinic oil is then stirred into this solution to form a white emulsion.

This emulsion can then be stirred into a liquid detergent concentrate.

EXAMPLE 3

The process of example 2 can be repeated except that a solution in a low boiling hydrocarbon of a waxy hydrocarbon is stirred into the azeotroped dispersion before emulsification in the coacervating polymer solution. The resultant stirred emulsion is then subjected to distillation under reduced pressure at a maximum temperature of 45° C. in order to strip off most of the low boiling solvent.

EXAMPLE 4

Savinase Plus Matrix Polymer Dispersion in Oil

An aqueous phase is formed by mixing 160 g 30% solution of a copolymer of styrene and ammonium acrylate with 140 g liquid Savinase preparation (12 g active protease enzyme, supplied by Novo-Nordisk A/S) and its pH is adjusted to 9.0).

The oil phase is formed by mixing 9 g polymeric inverse emulsifier, 12.7 g 60% amphipathic polymeric stabiliser, 107.9 g non-volatile hydrocarbon oil and 31.9 g volatile hydrocarbon solvent.

The aqueous phase is added to the agitated oil phase and then homogenised with a high shear Silverson mixer whilst maintaining the temperature of the emulsion below 40° C. After 30 minutes emulsification, extra 138.5 g of the volatile hydrocarbon solvent is added as a diluent.

The resultant emulsion is warmed to 30° C. and water/solvent mixture distilled under reduced pressure at a constant temperature about 30° C. The volume of water and solvent removed is monitored and distillation continued until no further water is collected in the distillate and then the temperature is allowed to rise to 110° C. under vacuum to remove remaining solvent. The dried dispersion is held at 100° C. for 15 minutes to drive off ammonia so as to render the matrix polymer insoluble in water.

The contents of the flask are cooled. The dispersion of Savinase plus polymer particles in oil (40% solids) is stable and having an average particle diameter of less than 1 μm.

EXAMPLE 5

Microencapsulation of Dispersion-in-Oil Obtained in Example 4

Diacetone acylamide (1 part) and acrylamide (0.4 part) were dissolved in 1% aqueous sodium acetate at pH 6.5 (4.2 parts). This solution was purged with nitrogen for 45 min in a lagged reaction vessel fitted with a mechanical stirrer.

Polymerisation was initiated by addition of 5% aqueous ammonium persulphate (500 ppm) followed by 5% aqueous sodium metabisulphite (500 ppm). The course of the reaction was monitored by recording the temperature. After 30 min the temperature had risen from 20° C. to a constant value of 70° C.

The mixture had become white and opaque and more viscous. On cooling a pale yellow clear viscous solution (25%) of Polymer A resulted.

By measuring the onset of turbidity of a 10% aqueous solution of Polymer A, the lower critical solution temperature (or temperature of reversible insolubilisation), was found to be 30° C.

The dried enzyme/polymer dispersion (33 parts) from Example 4 is added with high shear mixing to 100 parts 10% solution of Polymer A at pH 4.

The resultant smooth o/w emulsion is warmed in a water bath to 40° C. and held at this temperature for 15 min. Aqueous sodium sulphate (10%, 5 parts) is added and the mixture then allowed to cool slowly to 20° C. A stable microcapsule suspension in water is obtained having average particle size diameter of about 1 micron.

EXAMPLE 6

Demonstration of Partitioning and Dissolution Characteristics

Using the azeotropic distillation process as described in Examples 4 and 5, a dispersion comprising a dispersed phase of a styrene/acrylic polymer in a paraffinic oil is prepared. A water soluble polymeric dye (blue dextran) is incorporated into the polymer particle at 0.5% wt as a marker.

An experiment is performed to see if the polymer particles would activate (i.e., partition into and dissolve in the aqueous phase) on contact of matrix polymer plus dye dispersion with water at two different pH values.

The dispersion (1 part) was added with high shear mixing to water (99 parts) at either pH4 or pH9. After 2 min. mixing the turbid mixture was centrifuged with these results:

| pH | Observation | Conclusion |
| --- | --- | --- |
| 4 | Blue colour associated with oily layer Solution clear colourless | No activation |
| 9 | Distinct blue solution with a trace of oil on surface | Activation |

Therefore it can be seen that under acidic conditions the alkaline soluble polymer remains water insoluble and thus the particles stay in the oil phase.

We claim:

1. A liquid composition comprising a substantially stable dispersion in a liquid phase of particles having a size below 20 μm and having a substantially anhydrous core comprising a matrix polymer and a detergent enzyme distributed through the matrix polymer, and an outer shell deposited around the core of coacervated polymeric material that is impermeable to liquid detergent concentrates but which releases the enzyme when agitated in aqueous wash liquor.

2. A composition according to claim 1 in which the particles have been made by a process comprising forming a dispersion of an aqueous phase in a water immiscible liquid in the presence of a dispersion stabilizer wherein the aqueous phase comprises detergent enzyme and a solution or emulsion of a matrix polymer, and azeotroping the dispersion to convert the aqueous phase into particles comprising solid matrix polymer through which the detergent enzyme is distributed and the resultant particles are coated by coacervation with polymeric material.

3. A composition according to claim 2 in which the matrix polymer has been chemically modified during or after the azeotroping to render it less permeable to liquid detergent concentrate.

4. A composition according to claim 2 in which the particles also comprise a hydrophobic material between the coacervate coating and the matrix polymer particles formed by azeotroping.

5. A composition according to claim 2 in which the particles have been made by forming a dispersion in non-aqueous liquid of the matrix polymer particles containing enzyme, forming an emulsion of droplets of the dispersion in an aqueous medium containing coacervating polymeric material, and coating the droplets by coacervation of the coacervating polymeric material while dispersed in the aqueous medium to form a coacervate dispersion of particles comprising a core of solid matrix polymer through which enzyme is distributed and an outer coacervate coating.

6. A composition according to claim 5 in which the particles comprise a hydrophobic material between the core and the outer coacervate coating.

7. A composition according to claim 1 in which the matrix polymeric material is an addition polymer of ethylenically unsaturated ionic monomer optionally with ethylenically unsaturated non-ionic monomer.

8. A composition according to claim 1 in which the particles are below 3 μm in size.

9. A composition according to claim 1 in which the liquid phase is the liquid phase of a liquid detergent.

10. A composition according to claim 5 in which the liquid phase is the liquid phase of a liquid detergent.

11. A composition according to claim 1 in which the particles have a hydrophobic material disposed between the outer shell and the core.

12. A composition according to claim 1 in which the coacervated polymeric material is cross-linked.

13. A particulate composition that comprises particles having a substantially anhydrous core comprising a matrix polymer and a detergent enzyme distributed through the matrix polymer and an outer shell of coacervated polymeric material deposited around the core which releases the enzyme when agitated in wash liquor.

14. A particulate composition according to claim 13 having a hydrophobic oil between the core and coacervated polymer wherein the matrix polymer is sufficiently hydrophobic that it will partition preferentially into the oil rather than into water or an aqueous solution.

15. A composition according to claim 14 in which the particles have a size of below 20 μm and the composition is a liquid composition comprising a substantially stable dispersion of the particles in a liquid phase.

16. A composition according to claim 15 in which the liquid phase is the liquid phase of a liquid detergent and the coacervated polymeric material is impermeable to the liquid detergent.

17. A composition according to claim 16 in which the matrix polymer is a low critical solution temperature polymer that is soluble in aqueous wash liquor.

18. A composition according to claim 16 in which the coacervated polymer is a low critical solution temperature polymer that is soluble in aqueous wash liquor.

19. A composition according to claim 15 in which the particles have a size of below 3 μm.

20. A composition according to claim 15 in which the particles have been made by forming a dispersion in non-aqueous liquid of the matrix polymer particles containing enzyme, forming an emulsion of droplets of the dispersion in an aqueous medium containing coacervating polymeric material, and coating the droplets by coacervation of the coacervating polymeric material while dispersed in the aqueous medium to form a coacervate dispersion of particles comprising a core of solid matrix polymer through which enzyme is distributed and an outer coacervate coating.

* * * * *